(12) United States Patent
Glaug et al.

(10) Patent No.: US 6,443,934 B1
(45) Date of Patent: Sep. 3, 2002

(54) EFFICIENT THONG PANTILINER WITH FOLD-OVER ATTACHMENT MEANS

(75) Inventors: Frank S. Glaug, Chester Springs, PA (US); Kimberly Babusik, Wenonah, NJ (US)

(73) Assignee: Tyco Healthcare Retail Services AG (CH)

(*) Notice: Subject to any disclaimer, the term of this patent is extended or adjusted under 35 U.S.C. 154(b) by 0 days.

(21) Appl. No.: 09/965,169

(22) Filed: Sep. 27, 2001

(51) Int. Cl.[7] .......................... A61F 13/15; A61F 13/20
(52) U.S. Cl. .......................... 604/385.05; 604/385.04; 604/385.101; 604/387
(58) Field of Search .................. 604/327, 346–348, 604/354, 358, 365, 366, 369, 379, 380, 385.01, 385.03–385.08, 355.101, 355.14, 385.17, 385.19, 386, 387, 393–396, 328–331

(56) References Cited

U.S. PATENT DOCUMENTS

| | | | |
|---|---|---|---|
| 2,852,026 A | | 9/1958 | Karowski |
| 4,216,773 A | | 8/1980 | Ryan |
| 4,285,343 A | | 8/1981 | McNair |
| 4,496,359 A | * | 1/1985 | Pigenul ...................... 604/387 |
| 4,846,828 A | * | 7/1989 | Mendelsohn ................. 604/387 |
| 4,886,509 A | | 12/1989 | Mattsson |
| 4,900,319 A | | 2/1990 | Richwine |
| 5,037,417 A | | 8/1991 | Ternström et al. |
| 5,445,628 A | | 8/1995 | Gipson et al. |
| 5,454,803 A | | 10/1995 | Sageser et al. |
| 5,542,943 A | | 8/1996 | Sageser |
| 5,713,886 A | | 2/1998 | Sturino |
| 5,906,008 A | | 5/1999 | Heki et al. |

FOREIGN PATENT DOCUMENTS

| | | | |
|---|---|---|---|
| EP | 0511905 | * 11/1992 | ................. 604/387 |
| WO | 01/68024 | * 9/2001 | |

* cited by examiner

*Primary Examiner*—John G. Weiss
*Assistant Examiner*—Karin M. Reichle
(74) *Attorney, Agent, or Firm*—Caesar, Rivise, Bernstein, Cohen & Pokotilow, Ltd.

(57) ABSTRACT

A disposable absorbent article, e.g., pantiliner pad, for use with a thong shaped undergarment. The pad is of rectangular shape and includes a tapering, e.g., truncated triangle, absorbent core adhesively secured between a rectangular moisture pervious top sheet and a rectangular moisture impervious outer cover. Portions of the top sheet and outer cover extending beyond the margins of the core form a pair of triangular mounting flaps. The pad also includes adhesive stripes on the outer cover to secure the pad in place to the undergarment.

17 Claims, 2 Drawing Sheets

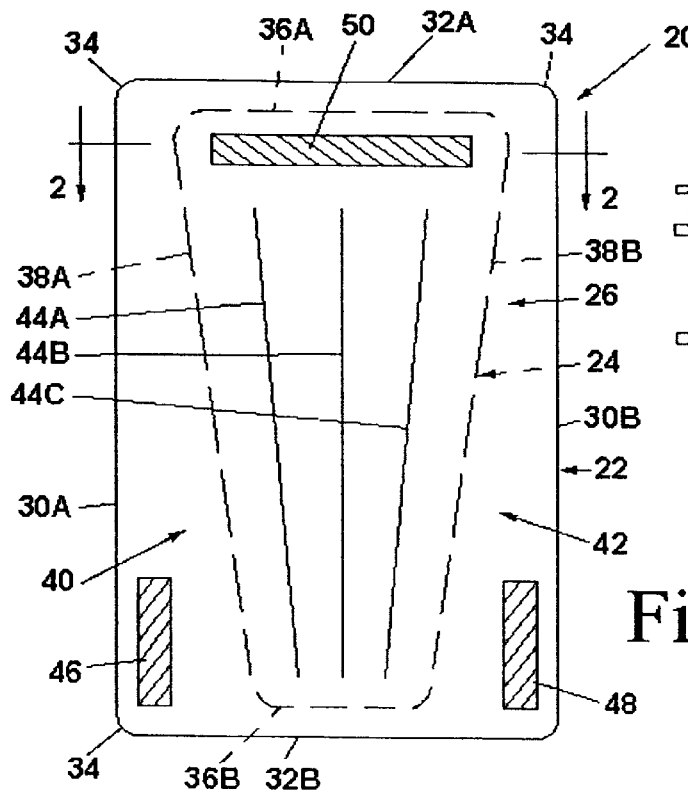
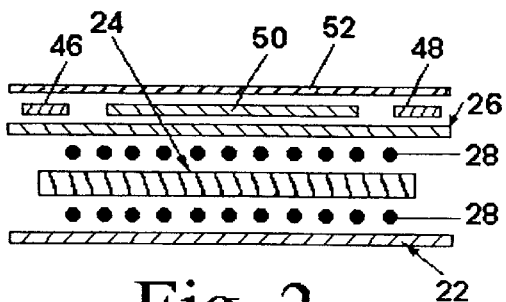
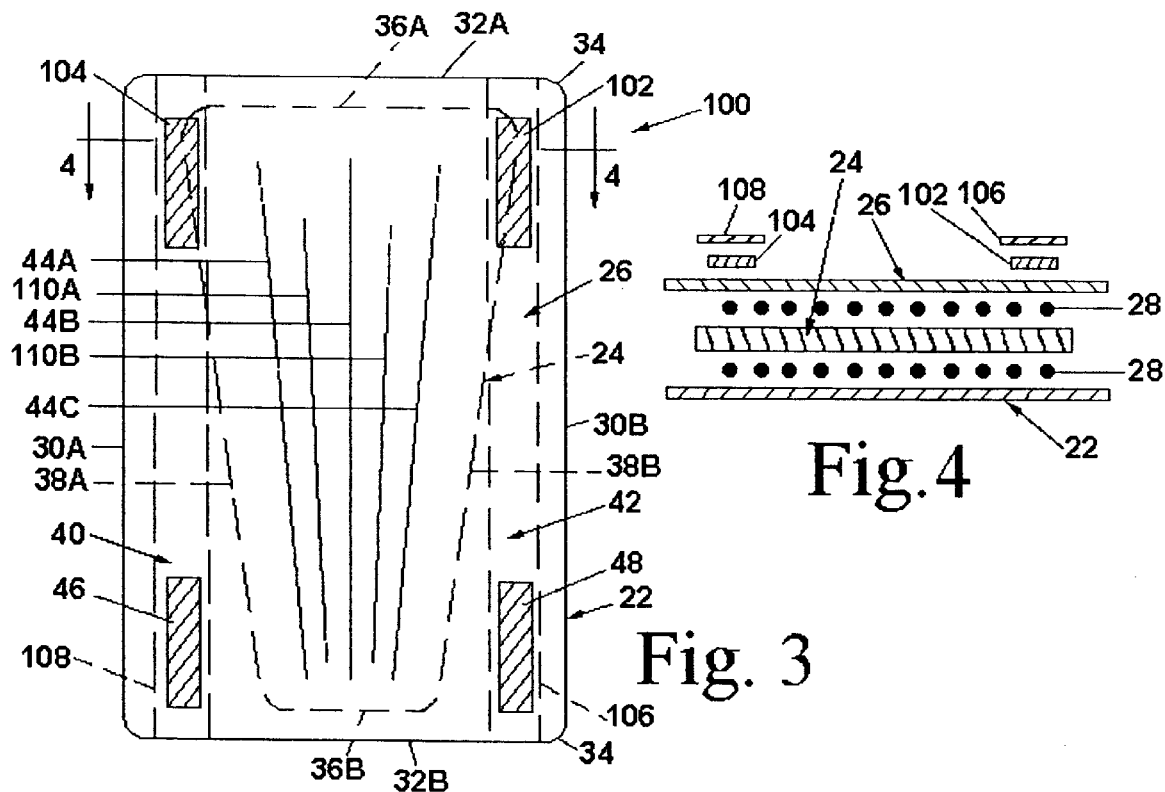
Fig. 1
Fig. 2
Fig. 3
Fig. 4

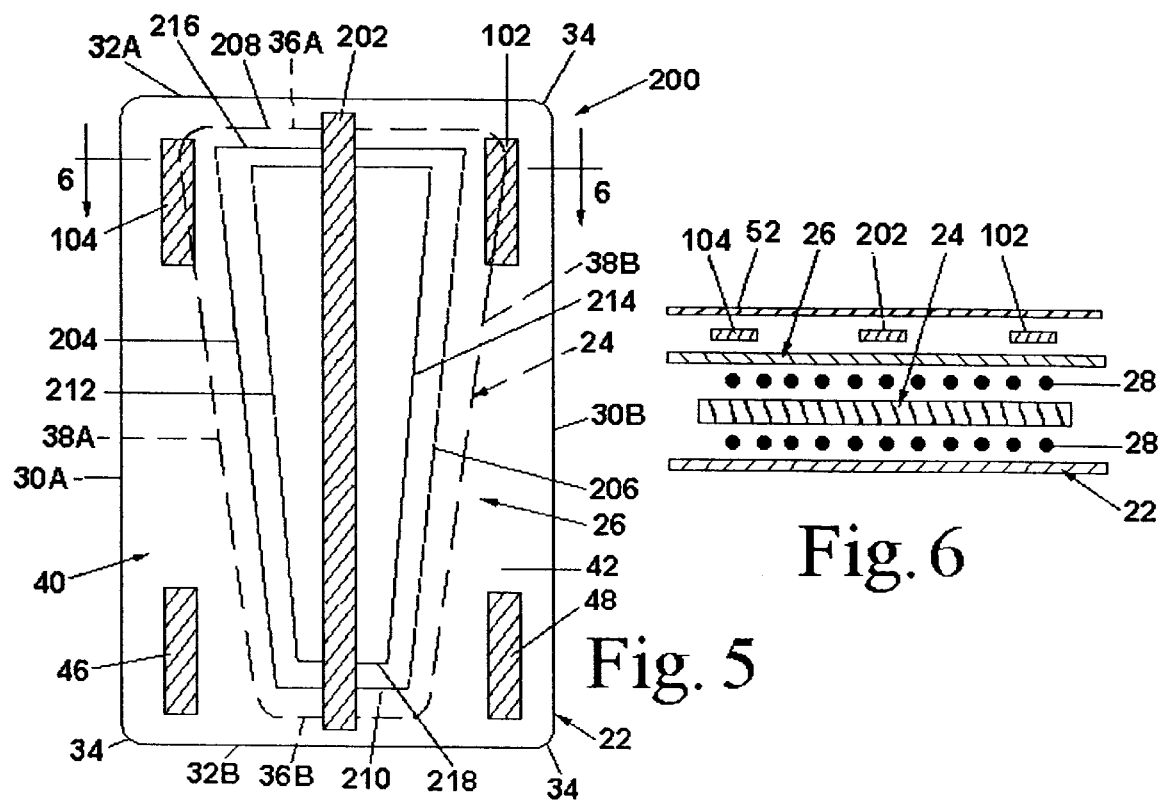
Fig. 5
Fig. 6
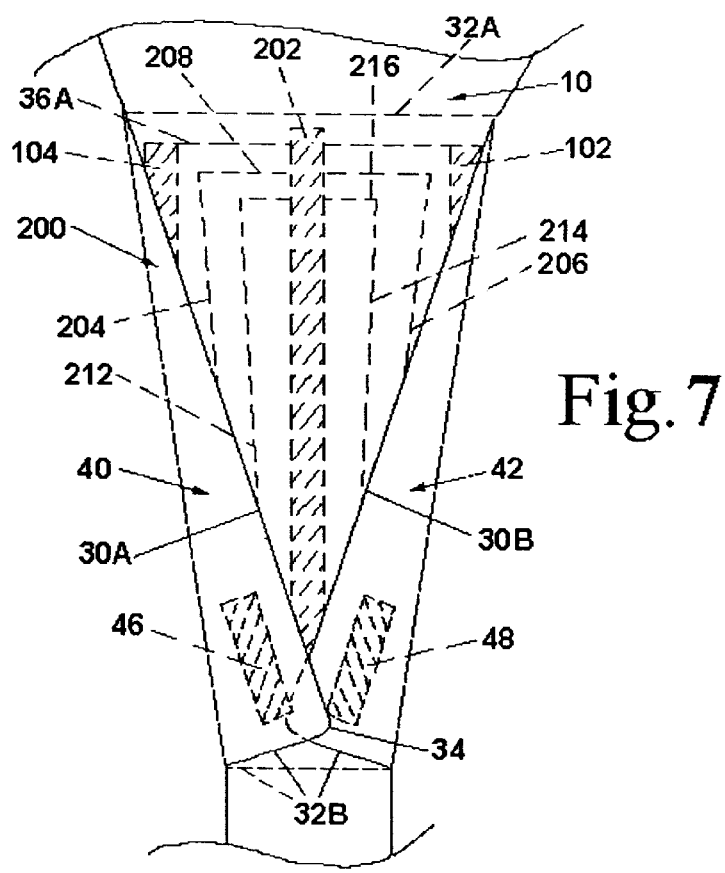
Fig. 7

US 6,443,934 B1

EFFICIENT THONG PANTILINER WITH FOLD-OVER ATTACHMENT MEANS

FIELD OF THE INVENTION

This invention relates generally to disposable absorbent articles and more specifically to disposable absorbent articles, e.g., light incontinent pads, light menstrual cycle pads, and the like for use with thong underwear, that are arranged to be readily secured to the underwear.

BACKGROUND OF THE INVENTION

Disposable absorbent sanitary articles, e.g., such as pantiliner pads, frequently make use of "flaps" or "wings" to facilitate securement of the pad to the interior surface of the crotch portion of underwear, e.g., panties or briefs. For example, U.S. Pat. No. 5,584,829 (Lavash et al.) discloses a sanitary napkin that has longitudinal side edges that naturally wrap the sides of a wearer's panties and are adhered thereto. The chassis shape is generally rectangular with an absorbent central core. As shown in FIG. 1, the absorbent core has a generally rectangular shape with rounded corners, slightly bowed ends and a somewhat narrowed waist in the center.

U.S. Pat. No. 5,713,886 (Sturino) discloses a panty liner especially for use with thong undergarments. The panty liner includes an absorbent core having first and second portions. The opposed sides of the second portion flare continuously from the sides of the first portion so that the second portion is wider than that of the first portion. A casing surrounds the absorbent core. One flap extends laterally from the casing adjacent the first portion of the absorbent core. Another flap extends laterally from the casing adjacent each of the opposed sides of the second portion of the absorbent core. An adhesive strip is secured to each of the flaps for attachment to the panties. The flaps are capable of being folded around the narrowed crotch portion of thong panties.

U.S. Pat. No. 4,216,773 (Ryan) discloses a disposable diaper having two longitudinal slits in the front end of a generally rectangular absorbent pad. Flaps are generated by fold lines originating on the edge of the pad at or near the rear corners and projected to intersect the adjacent slits at or near their inner ends. The flaps are folded inwardly to create a generally Y-shaped diaper having multiple layers of absorbent material in the area of heaviest wetting. The diaper is initially of a rectangular shape.

Other United States Letters Patents relating to pantiliner pads are: U.S. Pat. Nos. 2,852,026 (Karowski); 4,285,343 (McNair); 4,886,509 (Mattsson); 4,900,319 (Richwine); 5,037,417 (Ternstrom); 5,445,628 (Gipson); 5,454,803 (Sageser et al.); 5,542,943 (Sageser); and 5,906,008 (Heki et al.).

While all of the foregoing absorbent articles may be suitable for their intended purposes, they nevertheless leave something to be desired from the standpoints of ease of use, effectiveness, resistance to displacement, simplicity of construction, ease of manufacture and cost.

SUMMARY OF THE INVENTION

This invention relates to a disposable absorbent article, e.g., pantiliner or other absorbent pad, suitable for use with a thong-shaped undergarment to be worn by a wearer to trap and collect fluid waste products of the wearer. The pad is arranged to be releasably mounted to the crotch portion of the undergarment, with the crotch portion having an inner surface and an outer surface.

The pad is a thin, generally rectangularly shaped, generally planar member comprising a hydrophilic top-sheet, a moisture impervious outer cover sheet and a fluid absorbent core interposed between the top sheet and the outer cover sheet. The top sheet and the outer cover sheet are each of a generally rectangular shape and are coextensive in size. The top sheet and the outer cover sheet each have a pair of longitudinally extending marginal side edges, a transversely extending front edge and a transversely extending back edge. The core is of a generally wedge shape having a pair of marginal side edges, a transversely extending front edge and a transversely extending back edge.

The back edge of the core is disposed adjacent the back edges of the top-sheet and the cover sheet. The front edge of the core is disposed adjacent of the front edges of said top-sheet and the cover sheet. The marginal side edges of the core are disposed inward of the marginal side edges of the top-sheet and the cover sheet and taper from the front edge to the back edge, whereupon a pair of generally triangular foldable flaps extend outward of the marginal side edges of the core.

The outer cover includes first adhesive portions located in the area of the flaps for releasably mounting the pad on the inner surface of the undergarment with the first adhesive portions being arranged for engaging the outer surface of the undergarment. The pad may also include a second adhesive portion located on the outer cover in the area of the core and which is arranged for engaging the inner surface of the undergarment.

In accordance with one optional aspect of the invention the pad may include barrier lines in the core extending in a general longitudinal direction to deter migration of fluid laterally on the pad.

DESCRIPTION OF THE DRAWING

FIG. 1 is a bottom plan view of one embodiment of a thong pantiliner pad constructed in accordance with this invention after the release sheet (to be described later) has been removed;

FIG. 2 is an enlarged exploded sectional view, not to scale, taken along line 2—2 of FIG. 1, but showing the release sheet in place;

FIG. 3 is a bottom plan view, similar to FIG. 1, but of an alternative embodiment of a thong pantiliner pad constructed in accordance with this invention;

FIG. 4 is an enlarged exploded sectional view, not to scale, similar to FIG. 2, taken along line 4—4 of FIG. 3;

FIG. 5 is a bottom plan view, similar to FIGS. 1 and 3, of still another alternative embodiment of a thong pantiliner pad constructed in accordance with this invention;

FIG. 6 is an enlarged exploded sectional view, not to scale, similar to FIGS. 2 and 4, taken along line 6—6 of FIG. 5; and FIG. 7 is a bottom plan view of the crotch area of a thong panty having the pantiliner embodiment of FIG. 5 releasably mounted thereon.

DETAILED DESCRIPTION OF THE PREFERRED EMBODIMENT

Referring now to the various figures of the drawing wherein like reference characters refer to like parts, there is shown in FIG. 1 a disposable absorbent article 20 constructed in accordance with one embodiment of this invention. It should be pointed out that as used herein the term "disposable" means that article is designed to be used until soiled, either by urination or otherwise, and then discarded, rather than being washed and used again.

In the embodiment of FIG. 1 the article 20 is in the form of a pantiliner pad for thong shaped panties. While the following description will focus on thong-shaped pantiliners, it 20 should be clear that the subject invention can be used for any type of pad-like absorbent article to be worn by a person within an undergarment having a tapering crotch area for trapping urine or menses.

The pantiliner 20 basically comprises a thin generally planar structure. In particular, the pad may be any thickness in the range of 1.0 mm to 5.0 mm, with 2.5 mm being one preferred thickness for a pantiliner. As can best be seen in FIG. 2, the pad 20 is formed of a liquid pervious (hydrophilic) top sheet 22, a liquid absorbent, e.g., air-laid composite, core 24, and an liquid impervious outer cover sheet or moisture barrier 26. The top sheet 22 may be of any liquid pervious material. One particularly suitable material is a 13.5 gsm wettable non-woven coverstock, made of spun bond polypropylene, available from Avgol of Holon, Israel. The top sheet 22 is disposed on top of the absorbent core 24 and is secured thereon by a hot melt adhesive 28. One particularly suitable material for the adhesive is available from National Starch and Chemical of Bridgewater, N.J. under the trade designation #34-5634. The top sheet 22 may be formed of other material fibers (e.g., polyethylene, bi-component, polyester, rayon, cotton, etc.), fiber combinations (e.g., spunbond, air laid, wet laid, carded, thermal bonded, hydroentangled, etc.), and basis weights as well. In fact, if desired, the top sheet 22 may be formed of a liquid impermeable material, e.g., three dimensional polymeric film, having plural apertures or pores extending therethrough so as to make the material liquid permeable. One particularly suitable polymeric film is that disclosed in United States Design Letters Patent No. 362,120 and co-pending U.S. application Ser. No. 09/439,793, filed on Nov. 12, 1999, entitled "Absorbent article With Improved Fluid Acquisition System," which patent and application are both assigned to the same assignee as this invention and whose disclosures are incorporated by reference herein.

The outer cover 26 is disposed over the other side of the absorbent core 24, i.e., on the opposite side from the top sheet 22, and is secured thereon by a hot melt adhesive 28, like that which is used to secure the top sheet 22 to the core 24).

The outer cover 26 is preferably a hydrophobic material, e.g., plastic film or a laminate including a plastic film. Examples of plastic films are: polyethylene films, polypropylene films, co-extruded films (polyethylene and ethylene vinyl acetate), copolymer films (polyethylene/polypropylene), and polylaminates (polypropylene non-woven and polyethylene film). Still another example is a film made of a "breathable" microporous polyethylene. In one preferred embodiment of this invention the film is available from Tredegar Film Products of Richmond, Va., under the trade designation BF303W.

The core 24 can be made up of any suitable absorbent material, as well as combinations of different types of absorbent material(s). For example, in one preferred embodiment shown herein the absorbent core 24 is formed of an air-laid absorbent material, such as wood pulp, and which optionally can contain a super absorbent polymer powder (SAP) and a binder. Examples of SAP include polyacrylamides, polyvinyl alcohol, polyacrylates, various grafted starches, and the like. One particularly suitable super absorbent material is a cross-linked polysodium acrylate, which can be purchased from BASF Corporation, Portsmouth, Va., under the trade designation 2100A.

If desired the pad 20 may include a fluid acquisition or transfer layer (not shown) located between the inner layer 22 and the core 24. As is known, a fluid acquisition layer serves to manage, transport, accommodate and/or direct high volumes and flow rates of urine into the core. The fluid acquisition layer can be of any type construction, e.g., a thru-air bonded/carded web, a spunbond bicomponent non-woven web, a web of crosslink cellulosic fibers, apertured 3D (three dimensional) film, adhesive bonded fibers, or the like.

As can be seen in FIGS. 1 and 2 the top-sheet 22 and the cover sheet 26 are each of a rectangular shape having long side edges 30A and 30B, a short top edge 32A and a short bottom edge 32B. The side edges 30A and 30B extend linearly parallel to the central longitudinal axis of the pad 20, whereas the top and bottom edges, 32A and 32B, respectively, extend linearly perpendicularly to that axis. The top sheet 22 and cover sheet 26 are coextensive in size with each other so that their edges are coincident. All the corners of the top sheet 22 and cover sheet 26 are rounded at 34 and of the same radius of curvature.

The core 24 of the pad 20 is of a generally truncated triangular shape having a long top edge 36A, a pair of downwardly tapering side edges 38A and 38B, and a short bottom edge 36B. Each of the edges of the core is preferably linear. It should be pointed out at 15 this juncture that the core need not be a truncated triangular shape, but can be of any tapering shape (i.e., pear shape) conducive to use in the crotch area of a thong shaped or other narrow crotch undergarment.

The core 24 is located between the top sheet 22 and cover sheet 26 so that its top edge 36A is parallel but inwardly located with respect to the top edges 32A of those sheets. The bottom edge 36B of the core is also located but inwardly of the bottom edges 32A of the sheets 22 and 26. The side edges 38A and 38B of the core 24 are oriented at an acute angle to and inwardly of the side edges 30A and 30B of the top sheet 22 and cover sheet 26.

The areas of the adhesively secured top sheet 22 and cover sheet 26 which extend beyond the side edges 36A and 36B of the core 24 form a pair of generally triangularly shaped wings or flaps 40 and 42 as best seen in FIG. 1. These wings or flaps are foldable along lines coincident with or closely parallel to the side edges 36A and 36B of the core, to help secure the pad in place in the crotch region of the thong shaped panty, as will be described in detail hereinafter.

In order to prevent lateral migration of urine or other body fluids, e.g., menses, out of the pad from the side edges of the core, the pad 20 may optionally include plural, fluid-deterring barrier lines extending generally parallel to the side edges of the core. In the embodiment of FIG. 1 three such barrier lines 44A, 44B and 44C are provided. In the interest of drawing expediency and to better understand the construction of the pad, the barrier lines 44A, 44B and 44C are each shown by an unbroken line in FIG. 1, even though in that view they would not be visible through the outer cover 26.

The barrier line 44B extends along the central longitudinal axis of the pad 20 from a point closely adjacent the bottom edge of the core to a point below the top edge of the core. The barrier lines 44B and 44C extend generally parallel to the side edges of the core on either side of the central barrier line 44B.

Each of the barrier lines is produced by applying pressure and/or heat to the portions of the pad along the line to compress and increase the density of the materials along those lines, e.g., to compress the core 24. Depending upon the construction of the pad, the compression and/or heat applied to the materials making up the pad (particularly its core) causes the interstitial space between the individual fibers making up the core (any other layers of the pad composed of fibrous material) to compress or become densified to the point at which such densified areas are insufficient to allow liquid to flow therethrough. The application of pressure and heat can be accomplished using conventional thermal or ultrasonic bonding techniques or by pattern embossing. In some applications the use of pressure alone may be sufficient to produce a dense barrier line which remains after the pressure is removed. Moreover, an adhesive may be used when pressure is applied to create the dense barrier line. In fact, it is contemplated that water can be used in lieu of an adhesive for use with a core of suitable material so that after the pressure is released and the core dries the previously wet and compressed portions of the core will remain compressed, thereby forming the barrier lines.

The area of the pad 20 within the boundary defined by the barrier lines forms the "target area" for the fluid, e.g., urine and/or menses, insult, e.g., the point at which urine and/or menses first engages the pad. Irrespective of the point at which the fluid insult occurs within the target area the material making up the pad's core 24 will cause the fluid to spread out across the target area. Each barrier line will tend to prevent migration of the fluid across it and instead will tend to direct the fluid along it. Thus, the barrier lines will cooperate with each other to prevent or limit fluid migration or transfer out of the side edges of the core, while spreading the fluid out across a substantial area of the core to enable the pad to have a relatively high fluid capacity.

In order to releasably hold the pad 20 in place within the wearer's thong panty or other narrow, tapered crotch undergarment, the pad includes plural adhesive stripes 46, 48 and 50 of a "positioning" adhesive on the outer surface of the outer cover 26. The stripes 46 and 48 extend along the side edges 30A and 30B, respectively, parallel to those edges and close to the rounded corners 34 at the bottom edge 32B of the pad. The stripe 50 is longer in length than the stripes 46 and 48 and extends transversely, i.e., parallel to the top edge 32A at a central location between the two side edges 30A and 30B. Any suitable positioning adhesive can be used for the stripes, such as a pressure sensitive hot melt adhesive. One particularly suitable material for the positioning adhesive is available from National Starch and Chemical of Bridgewater, N.J., under the trade designation #34-591 A. In order to protect the positioning adhesive stripes 42,44 and 46 from degradation or being soiled by debris, a single release sheet 52, e.g., a release paper, (FIG. 2) of the same size and shape as the cover sheet 26 is releasably secured over the stripes on the cover sheet. In the interest of drawing simplicity the release sheet 52 is not shown in FIG. 1.

The release sheet 52 can be formed of any suitable adhesive-protective, yet easy to release, material. One particularly suitable material for the adhesive release sheet is available from Loparax of Willowbrook, Ill., under the trade designation ESP-39. The release sheet is arranged to be removed, e.g., peeled, from the cover sheet 26 to expose the adhesive stripes 46, 48 and 50. The pad 20 is now ready to be mounted on the thong shaped panty. The manner of mounting the pad 20 on the panty will be described in detail later. Suffice it for now to state that the pad is mounted on the inner surface of the crotch area of the panty so that portions of the adhesive stripes engage the inner surface of the panty's crotch area. The flaps 42 and 40 are then folded along the side edges 38A and 38B of the core 24 so that adhesive stripe portions on those flaps engage the outer surface of the panty's crotch area, thereby completing the releasable mounting of the pad 20 to the panty.

FIGS. 3 and 4 show an alternative embodiment of a pantiliner pad 100 constructed in accordance with this invention. The pad 100 is identical to the pad 20 except for the arrangement of the barrier lines, the number and orientation of the adhesive stripes and the use of respective release strips in place of a single unitary release sheet. In the interest of brevity the common components of the pads 20 and 100 will be given the same reference numbers and the details of their construction and operation will not be reiterated. Thus, as can be seen the pad 100 includes four mounting stripes 46, 48, 102 and 104. The stripes 102 and 104 are identical to the stripes 46 and 48 but are located on the outer cover adjacent the corners 34 at the top edge 32A of the outer cover and aligned with the stripes 46 and 48. The stripes 102 and 104 are located so that portions are disposed within the area bounded by the core 24 and portions are disposed in the area of the flaps 40 and 42, for reasons to be described later. Moreover, instead of using a common (single) release sheet, the pad 100 makes use of a pair of release elongated strips 106 and 108. The strips 106 and 108 are of a width slightly wider than the width of the stripes 46, 48,102 and 104, and are of the length of the pad 20. The location of these strips is shown by the broken lines in FIG. 3. Each of the strips 106 and 108 is located so that it overlies a respective one of the pair of stripes, e.g., strip 106 overlies adhesive stripes 48 and 102, while strip 108 overlies adhesive stripes 46 and 104. As will be appreciated by those skilled in the art to expose the adhesive stripes of the pad 100, all that is required is to peel the strips 106 and 108 off of the outer cover 26. The pad 100 is now ready for mounting on the panty as will be described later.

In the interest of deterring lateral leakage from the pad 100 it also includes densified barrier lines. In particular, pad 100 includes five barrier lines instead of three (as is the case with the pad 20). To that end, as shown in FIG. 3, the pad 100 includes two barrier lines 110A and 110B interposed between the barrier lines 44A, 44B, and 44C. The barrier lines 110A and 110B are slightly shorter than the lines 44A, 44B, and 44C. All of these barrier lines are shown by unbroken lines in that figure in the interest of better understanding of the structure of the pad 100, even though they would not be visible through its outer cover 26.

FIGS. 5 and 6 show another alternative embodiment of a pantiliner pad 200 constructed in accordance with this invention. The pad 200 is identical to the pad 100 except for the arrangement of the barrier lines, the number and orientation of the adhesive stripes and the use of a unitary release sheet in place of the respective release strips of that figure. In the interest of brevity the common components of the pads 200 and 100 will be given the same reference numbers and the details of their construction and operation will not be reiterated. Thus, as can be seen the pad 200 includes five mounting stripes 46, 48, 102, 104 and 202. The stripe 202 is identical to the other stripes except that it extends almost for the length of the pad and is centered along the central longitudinal axis of the outer cover 26. Moreover, instead of using a pair of release strips 106 and 108, like in the embodiment 100, the pad 200 uses a common (single) release sheet 52, like that of embodiment 20. Thus, to expose the adhesive stripes of the pad 200, all that is required is to peel the release sheet 52 off of the outer cover 26. The pad 200 is now ready for mounting on the panty as will be described later.

In the interest of deterring lateral leakage from the pad 200, it also includes plural densified barrier lines. These lines extend generally parallel to the core's side edges 38A and 38B, but also include transversely extending line portions. In particular, as best seen in FIG. 5, the pad 200 includes barrier lines 204, 206, 208, 210, 212, 214, 216 and 218. The barrier lines 204 and 206 extend generally parallel to the core's side edges 38A and 38B, respectively. The line 208 is a transversely extending line which connects the top ends of the lines 204 and 206. The line 210 is a transversely extending line which connects the bottom end of the lines 204 and 206. In a similar manner, the barrier lines 212 and 214 extend generally parallel to the core's side edges 38A and 38B, respectively. The line 216 is a transversely extending line which connects the top ends of the lines 212 and 214. The line 218 is a transversely extending line which connects the bottom end of the lines 212 and 214. The lines 212, 214, 216 and 218 are located within the area bounded by the lines 204, 206, 208 and 210. As should be appreciated by those skilled in the art the inclusion of the transversely extending barrier lines will enhance fluid retention by the pad 200 by deterring leakage of fluid from the ends 36A and 36B and from the sides 38A and 38B of the pad.

The mounting of any of the pads constructed in accordance with this invention, e.g., pad 200, onto the thong shaped panty 10 will now be described. To that end the release sheet 52 is peeled off of the outer cover to expose the pad's adhesive stripes 46, 48, 102, 104 and 202. The pad 200 is then oriented so that its outer cover 26 is disposed over the inner surface of the crotch area of the thong shaped panty 10 like shown in FIG. 7. The pad is then brought into engagement with that surface, whereupon the central adhesive stripe 202 and portions of the stripes 102 and 104 releasably adhesively engage that surface. The flaps 40 and 42 are then folded along the side edges 38A and 38B of the core 24 so that one of the adhesive stripes 46 and 48 releasably adhesively engages the outer surface of the crotch portion of the panty, while the adhesive strip of other flap releasably adhesively engages that surface and a portion of the first flap. For example, as shown in FIG. 7 the flap 42 is folded first, whereupon the adhesive stripe 48 on it engages the outer surface of the panty. Then the other flap 40 is folded so that its adhesive stripe 46 engage a portion of the outer surface of the crotch area of the panty as well as a portion of the flap 42. Portions of the stripes 102 and 104 will also engage the outer surface of the crotch area of the panty. The amount of overlap of the flaps and the amount of the portions of the adhesive stripe 102 and 104 which engage the outer surface of the panty will be a function of the point at which the flaps are folded and the width and angle of the marginal edges of the thong pantiliner crotch.

As should be appreciated by those skilled in the art the construction and arrangement of the pantiliner pads of this invention when mounted in place on the undergarment will closely conform to the anatomy of the wearer, without bunching up or roping on the thin crotch portion of the undergarment, thereby resulting in a comfortable fit. Moreover, the folded flaps and their releasable adhesive securement to the crotch of the thong shaped panty will tend to prevent movement or shifting of the pad, thereby further enhancing comfort, while tending to be less prone to side leakage. In regard to the latter, the folded flaps themselves will tend to prevent the lateral migration of liquid from the pad, even if the optional fluid barrier lines are not utilized. Moreover, since the top sheet and cover sheet are each rectangular in shape, the pads of this invention can be readily fabricated without wastage of material (as characterizes the prior art). In addition the resulting pad is quite simple in construction. Further still since the pad is rectangular it can be readily packaged in conventional rectangular shaped boxes or other packaging. These factors contribute to significant manufacturing/packaging economies.

Without further elaboration the foregoing will so fully illustrate the invention that others may, by applying current or future knowledge, adopt the same for use under various conditions of service.

We claim:

1. A disposable absorbent pad for use with a thong-shaped undergarment having a crotch portion and trapping and collecting fluid waste products that is arranged to be secured to the crotch portion of the thong-shaped undergarment, the crotch portion of the undergarment having an inner surface and an outer surface, said pad being a thin, generally rectangularly shaped, generally planar member comprising a hydrophilic top-sheet, a moisture impervious outer cover sheet and a fluid absorbent core interposed between said top sheet and said outer cover sheet, said top sheet and said outer cover sheet each being of a generally rectangular shape and coextensive in size, said top sheet and said outer cover sheet each having a pair of longitudinally extending marginal side edges, a transversely extending front edge and a transversely extending back edge, said core being of a generally wedge shape having a pair of marginal side edges, a transversely extending front edge and a transversely extending back edge, said back edge of said core being disposed adjacent said back edges of said top-sheet and said cover sheet, said front edge of said core being disposed adjacent of said front edges of said top-sheet and said cover sheet, said marginal side edges of said core being disposed inward of said marginal side edges of said top-sheet and said cover sheet and tapering from said front edge to said back edge, whereupon a pair of generally triangular foldable flaps extend outward of said marginal side edges of said core, said outer cover including first adhesive portions located in the area of said flaps for releasably mounting said pad on the inner surface of the undergarment with said first adhesive portions being arranged for engaging the outer surface of the undergarment.

2. The pad of claim 1 wherein said back edge of said core is shorter than said back edge of said top sheet and cover sheet.

3. The pad of claim 1 wherein said front edge of said core is shorter than said front edge of said top sheet and cover sheet.

4. The pad of claim 3 wherein said back edge of said core is shorter than said back edge of said top sheet and cover sheet.

5. The pad of claim 1 wherein said marginal side edges of said core are each linear.

6. The pad of claim 1 wherein said top sheet is hydrophilic.

7. The pad of claim 6 wherein said top sheet is a non-woven material.

8. The pad of claim 1 wherein said outer cover sheet is a plastic film.

9. The pad of claim 1 additionally comprising a second adhesive portion located on said outer cover sheet in the area of said core arranged for engaging the inner surface of said undergarment.

10. The pad of claim 9 additionally comprising a release sheet wherein said release sheet is releasably secured over said adhesive portions.

11. The pad of claim 9 additionally comprising a pair of release sheets, one of said release sheets being releasably secured to one of said first adhesive portions and the other of said pair of release sheets being releasably secured to another of said first adhesive portions.

12. The pad of claim 11 wherein each of said pair of release sheets is also releasably secured over said second adhesive portion.

13. The pad of claim 9 wherein said first adhesive portions comprise at least one adhesive patch located on said outer cover in the area of one of said flaps and at least another adhesive patch located on said outer cover in the area of the other of said flaps, and wherein said second adhesive portion comprises at least one adhesive patch located on said outer cover in the area of said core.

14. The pad of claim 13 wherein each of said adhesive patches is in the form of a stripe extending generally parallel to said marginal sides of said top sheet and said outer cover.

15. The pad of claim 14 wherein said second adhesive portion comprises at least three adhesive stripes on said outer cover, one of said stripes being located in approximately the center of said core, the other two stripes being located partially in the area of said core and partially in the area of said flaps.

16. The pad of claim 1 additionally comprising a release sheet releasably secured over said first adhesive portions.

17. The pad of claim 1 wherein said core includes plural densified lines to deter lateral migration of fluid from the pad.

* * * * *